United States Patent [19]

Khalafalla

[11] Patent Number: 4,813,952
[45] Date of Patent: Mar. 21, 1989

[54] CARDIAC ASSIST DEVICE

[75] Inventor: Aida S. Khalafalla, Minneapolis, Minn.

[73] Assignee: Medtronic, Inc., Minneapolis, Minn.

[21] Appl. No.: 135,791

[22] Filed: Dec. 21, 1987

Related U.S. Application Data

[63] Continuation of Ser. No. 761,252, Aug. 1, 1985, abandoned.

[51] Int. Cl.$^4$ ............................................... A61F 2/22
[52] U.S. Cl. ......................................................... 623/3
[58] Field of Search ............................................. 623/3

[56] References Cited

U.S. PATENT DOCUMENTS

| 4,078,267 | 3/1978 | Cieszyushi | 623/3 |
| 4,105,016 | 8/1978 | Donovan | 623/3 |
| 4,240,409 | 12/1980 | Robinson et al. | 623/3 |
| 4,536,893 | 8/1985 | Parravicini | 623/3 |
| 4,652,265 | 3/1987 | McDougall | 623/3 |

OTHER PUBLICATIONS

"Biophysical Studies on Nerve and Muscle", *BioPhysics: Concepts and Mechanisms*, New York: Reinhold Pub., Chapter 10, 1962, pp. 262-294 by E. J. Casey.
*Biomechanical Cardiac Assist Cardiomyoplasty and Muscle-Powered Devices*, Chapters 2, 3, 5, 6, 11 and 12, Edited by Ray C. J. Chiu, M.D., Ph.D., 1986.
"The Experimental Use of the Diaphragm as an Auxiliary Myocardium", *Surgical Forum 9*, 266-268, 1958, by Kantrowitz and McKinnon.
"Graft of the Diaphragm as a Functioning Substitute for the Myocardium; An Experimental Study", *The Journal of Surgical Research*, vol. IV No. 10, Oct. 1964, by Nakamura and Glenn, pp. 435-439, 1964.
"Synchronously Stimulated Skeletal Muscle Graft for Myocardial Repair", *The Journal of Thoracic and Cardiovascular Surgery*, vol. 87, No. 3, Mar. 1984, by Dewar, Drinkwater, Wittnich and Chiu, pp. 325-331.
"Muscle Energy for Total Artificial Heart Drive", Thona et al. *Artificial Organs*, vol. 5 (Suppl), pp. 441-445, 1981.

*Primary Examiner*—Richard J. Apley
*Assistant Examiner*—James Prizant
*Attorney, Agent, or Firm*—Robert C. Beck; John L. Rooney; Joseph F. Breimayer

[57] ABSTRACT

A muscle-powered pump to assist the natural heart is disclosed. The device comprises an oblate, spheroidal-shaped pumping chamber surrounded by innervated muscular tissue. The device may be coupled to the ventricle and descending aorta with valves and be stimulated in synchrony with the natural depolarization of the heart or the device may be inserted into the descending aorta and used as a counter pulsation device. In this application, the innervated muscle is stimulated after a brief delay from the natural cardiac depolarization.

8 Claims, 4 Drawing Sheets

CARDIAC ASSIST DEVICE

This is a continuation of co-pending application Ser. No. 761,252, filed on Aug. 1, 1985, now abandoned.

BACKGROUND OF THE INVENTION

The present invention relates to a totally implantable muscle-powered cardiac assist device to be used as an auxiliary pump in conjunction with the natural heart. In one configuration the device comprises a pair of tubular shunts coupled to the aorta and left ventricle of the heart which communicate with an elastic chamber formed in the shape of an oblate ellipsoid. Valves located within the shunts permit blood to flow from the weak or damaged left ventricle of the heart into the aorta when the elastic chamber is compressed. An alternate configuration involves the use of the elastic chamber as an extra-aortic counterpulsation device with no valve requirement.

The mechanical energy required to compress the chamber is supplied by an innervated autogenous muscle surrounding the elastic chamber. This muscle is stimulated by an implantable pulse generator in synchrony with the ventricular depolarization of the patient's heart. In operation, the contraction of the elastic chamber under the influence of a muscle tissue forces blood into the aorta. Additionally, the pulse generator provides chronic ultra-low frequency stimulation to the muscle tissue to maintain a high population of slow twitch-type muscle fibers.

The use of autogenous muscle to drive mechanical pumps is known in the art from U.S. Pat. No. 4,078,267 which discloses an artificial heart propelled by respiratory muscles. Devices of this type have enjoyed only limited success because, mammalian skeletal muscle is not capable of long-term pumping due to metabolic fatigue. Recently it has been demonstrated that chronic electrical stimulation of muscle tissue produces an adaptive transformation of muscle tissue which increases the capillary densitiy in the muscle tissue as well as the mytochondrial volume and results in an increased work capacity of the transformed muscle. Histologically, such tissue is transformed to the slow twitch-type which exhibits greatly increased resistance to fatigue.

Early experimental evaluation of skeletal muscles for myocardial augmentation was reported by Kantrowitz and McKennon. See *Experimental Use of the Diaphragm as an Auxiliary Myocardium*, Surgical Forum 9, Page 266, 1959. By wrapping diaphragm muscle around the heart and stimulating it via the phrenic nerve, they observed no significant hemodynamic effects; however, when employed as the counterpulsation device, they noted a short-term increase in the diastolic aortic pressure. Later, in 1964 Nakamora and Glenn utilized the diaphragm to assist atrial function. The diaphragm graft in the atrium continued to contract in response to stimulation from the phrenic nerve and served to elevate the right atrial pressure chronically. See *Graft of the Diaphragm as a Functioning Substitute for the Myocardium; an Experimental Study*, J Surg Res 4; 435, 1964.

Other approaches which involve the use of small spring-loaded diaphragm pumps with externally positioned flap valves have been energized by canine quadricept femorous muscles. Mechanical pumps of this type have shown outputs of 600–700 milliliters per minute.

These early studies demonstrated the potential for the use of skeletal muscles to augment ventricular action of the heart. However, this initial work indicated that a critical problem existed in the deterioration of muscle performance with continued use. Attempts at improving the hemodynamic behavior of the muscle graft by lower frequency stimulation was demonstrated by Doer, et al in 1984. See *Synchronously Stimulated Skeletal Muscle Graft for Myocardial Repair*, J Thorac Cardiovasc Surg 87: 325, 1984. These more recent studies demonstrated that skeletal muscle, while initially capable of hemodynamic work, fatigues rapidly even under conditions less demanding than those which are tolerated indefinitely by the cardiac muscle itself.

Although skeletal muscles contain populations of fibers which share many of the characteristics of cardiac muscle tissue, the skeletal type (I) or slow twitch fibers serve primarily a postural role in that they are required to sustain prolonged periods of activity without appreciable fatigue. However, in the tissue suitable for application to cardiac assist devices, these fibers are interspersed with at least an equal number of fast or type (II) fibers. These latter fibers have the properties suited to brief periods of intense activity, their fast contractile characteristics derive from specific contractile protein isoforms and extensive sacrotubular system and their dependence on energy derived from anaerobic glycolysis. This metabolic substrate renders the muscles susceptible to fatigue under conditions of prolonged use even at low cardiac rate duty cycles such as those demonstrated by Doer. Additionally, unlike cardiac muscle cells which contract as a synctyium, skeletal muscle fibers are normally recruited to an extent determined by the intensity of activation and in a fixed sequence. In practice, the fast fibers are the first to contract and the slow fibers are the last to contract. This structural property of the skeletal muscles minimizes the functional demand placed upon the fibers which are most susceptible to fatigue. However, the application of such tissues to cardiac assist devices require that all of the muscle tissues be recruited simultaneously and be equally active with the consequence of chronic fatigue.

Over the past fifteen years, however, a plasticity of muscle fiber type has been demonstrated in response to chronic electrical stimulation. In 1969, Salmons, et al demonstrated that the contractile speed of fast muscles could be modulated to a striking extent by continuous electrical stimulation of the motor nerve at a frequency of 10 Hz.

There is now a large body of evidence to show that fast skeletal muscles can ultimately acquire all of the physiological, biochemical, and ultrastructural characteristics of slow muscle under conditions of chronic stimulation. Such adapted muscles demonstrate a corresponding increase in the use of enzymes for aerobic metabolism and a decrease in the enzymes for glycolysis.

When a change is also involved, the contractile proteins period is reflected by an increased conversion of light to heavy chain insoforms of myosin characteristic of slow muscle tissue. As these changes progress over a period of months, the muscle mass contracts progressively more slowly and is more resistant to fatigue than initially. These recent developments have suggested that appropriately adapted skeletal muscle may be harvested to restore myocardial function through surgical procedures.

In the present application, however, chronically stimulated and transformed muscle tissue is utilized to actuate a biological pump implanted within the body and connected to the aorta for assisting a weakened or diseased ventricle in the delivery of blood to body tissues. At the present time, it is contemplated that the latissimus dorsi muscle will be dissected from the patient's back through a posterial aterial incision and mobilized, preserving its vascular and nervous structure. This pedicle will be passed into the thorax through a window created by the resection of approximately a 3 cm segment of the lateral arc of the second rib, thus permitting the insertiion of the pedicle into the thorax. The posterial lateral incision is closed, and access to the pedicle is achieved through a median sternotomy. The muscle flap will then be stretched along its striated side and wrapped around the elastic pumping chamber and closed at both ends using superficial interrupted sutures. After stretching the muscle flap around the elastomeric balloon, electrodes are then expected to be implanted, either on the nerve of the latissimus dorsi or through the muscle or both. The electrode system would then be attached to a suitable cardiomystimulator.

In this context, the present invention is directed to an optimized biological pump which exploits the ability of transformed tissue to augment the ventricular action of the heart. This invention discloses two alternate embodiments to achieve the desired goal of a totally implantable, body-compatible cardiac assist system.

DETAILED DESCRIPTION OF THE INVENTION

Figure 1:
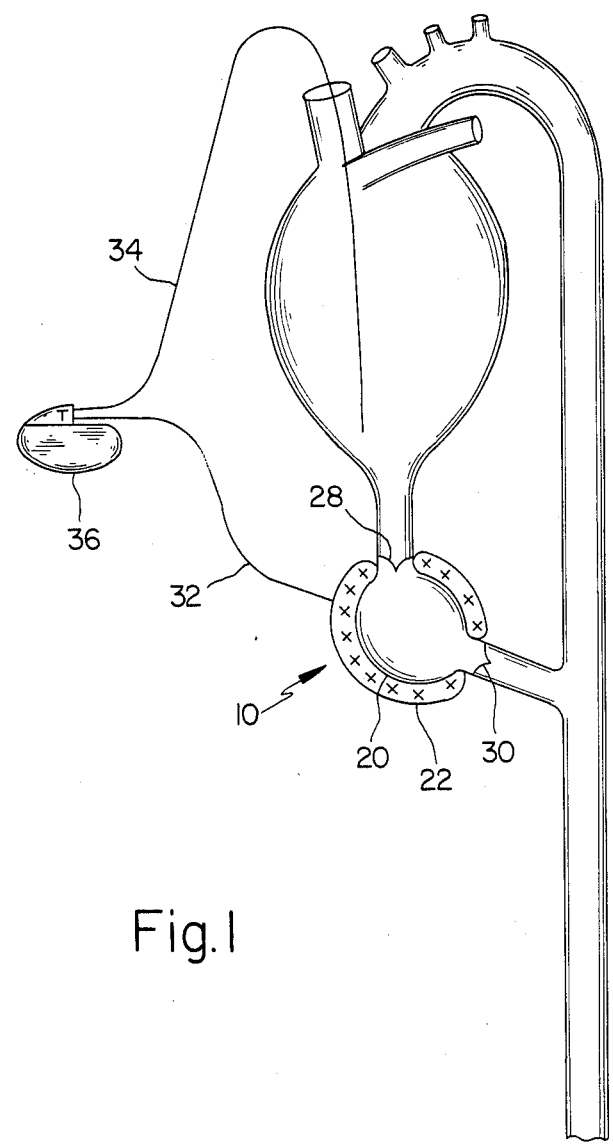
FIG. 1 is a cross-section of the Apico-Aortic Conduit System (AACS) embodiment of the invention.

I. The first embodiment is referred to as a Apico-Aortic Conduit System (AACS), depicted in FIG. 1 at 10; and, the second embodiment is referred to as an Extra-Aortic Balloon Counterpulsation System (EABC) and is shown in the FIGS. 2, 3 and 4.

In either embodiment, the pump consists of an elastomeric chamber 20, surrounded by a muscle sheath 22, formed from transformed muscle tissue. The chamber is shaped in the form of an oblate ellipsoid having a horizontal axis 26 and a vertical axis 24. In the AACS system, unidirectional heart valves 28, 30 may be provided to establish the flow direction of blood through the chamber. These values are located in apertures formed in the periphery of the elastomeric chamber. Valves suitable for this application include the Medtronic mitral heart valve Model 7700 having an orifice diameter of 2 cm for the entry valve 28. A valve suitable for the exit valve 30 of the chamber is the Medtroniac aortic heart valve Model A7700 having an orifice diameter of 1.6 cm.

The elastic chamber is shaped in the form of an ellipsoid of revolution. The generating ellipse has a major or horizontal axis 26, which is the axis of revolution and a minor or vertical axis 24 as shown in the Figure. For a desired fluid stroke volume of 70 cc, the chamber should have a volume of approximately 140 cc. This is based upon an assumed ejection ratio of 50%. For a volume of 140 cc, the dimensions of the major and minor axes are related by $b = 5.78/\sqrt{a}$.

To compute the minimum force required to pump the desired stroke volume, one may model the chamber as an equivalent cylinder, having a volume equal to the chamber, whose length is equal to the horizontal axis of the ellipse. In this instance, the cylinder will have a base radius $\bar{b}$ given by $\bar{b} = 4.72/\sqrt{a}$. The force required to displace the desired blood volume is given by: $(70/\tau \bar{b})^2 (\rho/\pi) = 602.95a$ where $\tau$ is the ejection time (0.35 sec) and $\rho$ is the specific gravity of blood (1.055). This force corresponds to the end pressure or terminal pressure, $P_{ter}$, in the chamber distributed over the exit aperture of the chamber as determined by the size of the aortic valve aperture, $r_o$.

In practice, sufficient muscle mass is wrapped around the balloon to generate a static pressure of 120 mm of mercury or $1.6 \times 10^5$ dynes per square, centimeter within the chamber. This is the available pressure, $P_{avl}$, responsible for driving blood into the body systemic vessels.

The mass flow rate for a Newtonian fluid in the laminar regime is given by Poiseuille expression $$f = \frac{\pi P r^4}{8 L \eta},$$

where P is the pressure, L is the length of the tube, r is the tube radius, and $\eta$ is the viscosity coefficient. As previously mentioned, the available pressure responsible for driving the fluid out of the pump is related to the radius of the aortic valve as indicated by the relationship above. Likewise, the minimum pressure or terminal pressure in the chamber is related to the average radius of the balloon which is taken as the radius of the equivalent cylinder. The quantity $Pr^4$ in the Poiseuille relation gives an estimate of the system compliance, and therefore, to achieve maximum compliance matching, we should have $P_{avl} \times r^4 = P_{ter} \times (\bar{b})^4$. This leads to: a $r_o^6 = 0.595$. For an aortic valve orifice, $r_o$, of 0.8 cm, we have $a = 2.27$ cm and $b = 3.84$ cm for the desired dimensions of the oblate ellipsoid.

Optimization of the chamber size is based on a fluid flow rate, f, expressed in cc's per second, which is equal to the systolic's cardiac output of the cardiac assist device. The parameters should be optimized to provide a stroke volume of 70 cc, an ejection time of 350 ms and a volume flow rate of 200 cc per second. The fluid velocity is given by the flow rate divided by the cross-sectional area, A. Therefore, the average flow velocity during systolic time, $\bar{v} = f/A = 2.86a$. At the end of the ejection time, the fluid flow velocity within the chamber must become zero.

With respect to the muscle mass 22 required in this cardiac assist device, one can use Young-LaPlace equation to compute the tension required at the wall of the chamber to generate the 120 mm of mercury pressure. For a cylindrical balloon of unit radius, the wall tension is computed to be $1.6 \times 10^5$ dyne per centimeter. Measurements of muscle fibers reveal that the isometric force generated by a tensed muscle is approximately $2.9 \times 10^3$ grams per square centimeter of muscle cross-section or $2.9 \times 10^6$ dynes per square centimeter of muscle cross section. See Casey, E. J.; *"Biophysics, Concepts and Mechanisms,"* Reinhold Books, New York, 1962, p 262-294. Calculations for a cylindrical balloon of unit radius (R=1 cm) and sufficient length to accommodate at least 70 ml of blood leads to the following two useful rules of thumb:

Rule 1:

$$M = 2 \times 10^{31\ 3} RP$$

Where M is the muscular mass in grams, R is the balloon or bladder radius in cm, and P is the balloon pressure in dynes/cm$^2$.

Rule 2:

$$r_o{}^6 R^{-2} P = 4 \times 10^3$$

where $r_o$ is the radius of the tube connecting the balloon to the aorta.

For example, in order to achieve the human systolic pressure of 120 mm Hg ($1.6 \times 10^5$ dynes/cm$^2$) in a 70 ml balloon of radius R=1 cm, the required muscle mass is about 320 gm (11.3 oz.) according to Rule 1. Also, the radius, $r_o$ of the aortic valve, is estimated as 0.5 cm (0.2 inch from Rule 2).

By imposing an $r_o$ value of 0.8 cm and ejection ratio of 50% on the design parameters, it can be shown that the muscle mass required to wrap around the two caps of the oblate ellipsoid of volume 140 cm$^3$ is approximately twice that required for a volume of 70 cm$^3$, i.e., 645 gm (23 oz.).

II—The Extra-Aortic Balloon Counterpulsation Pump (EABC)

Figure 2:
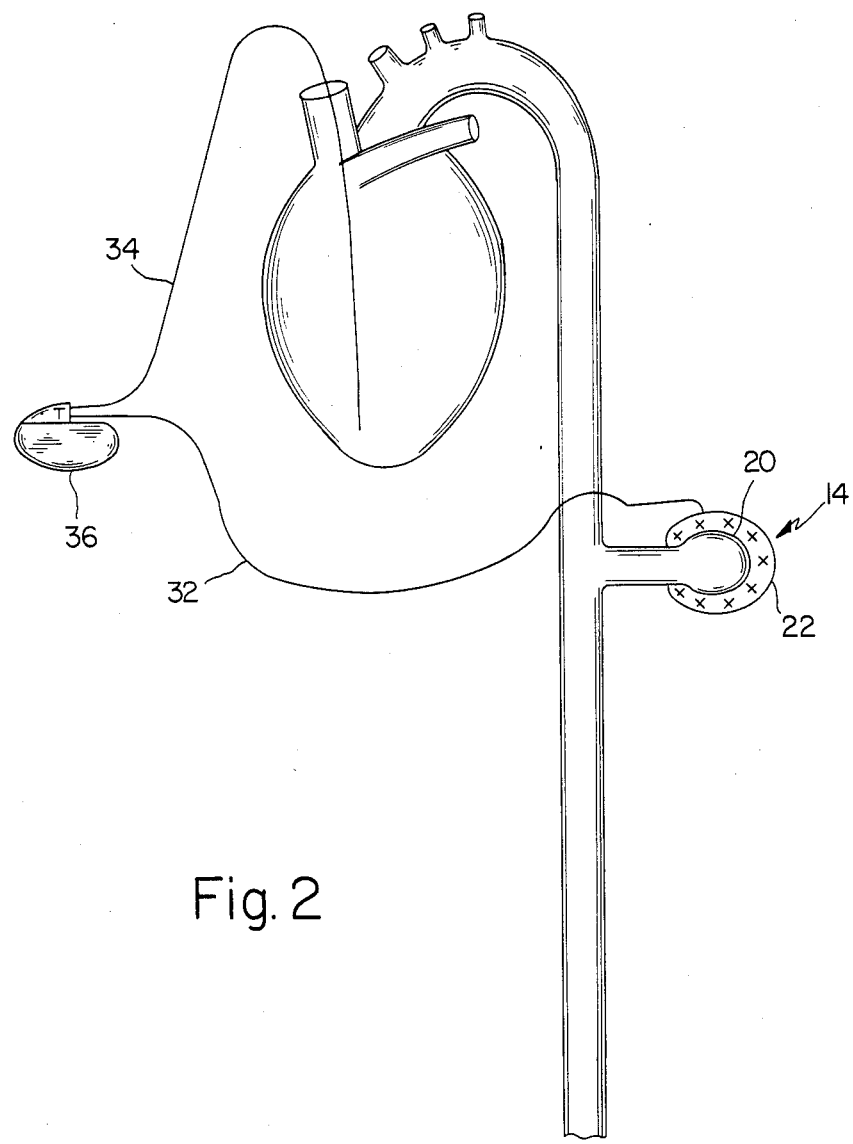
FIG. 2 is a cross-section of an extra aortic balloon counterpulsation EABC embodiment of the invention.
Figure 4:
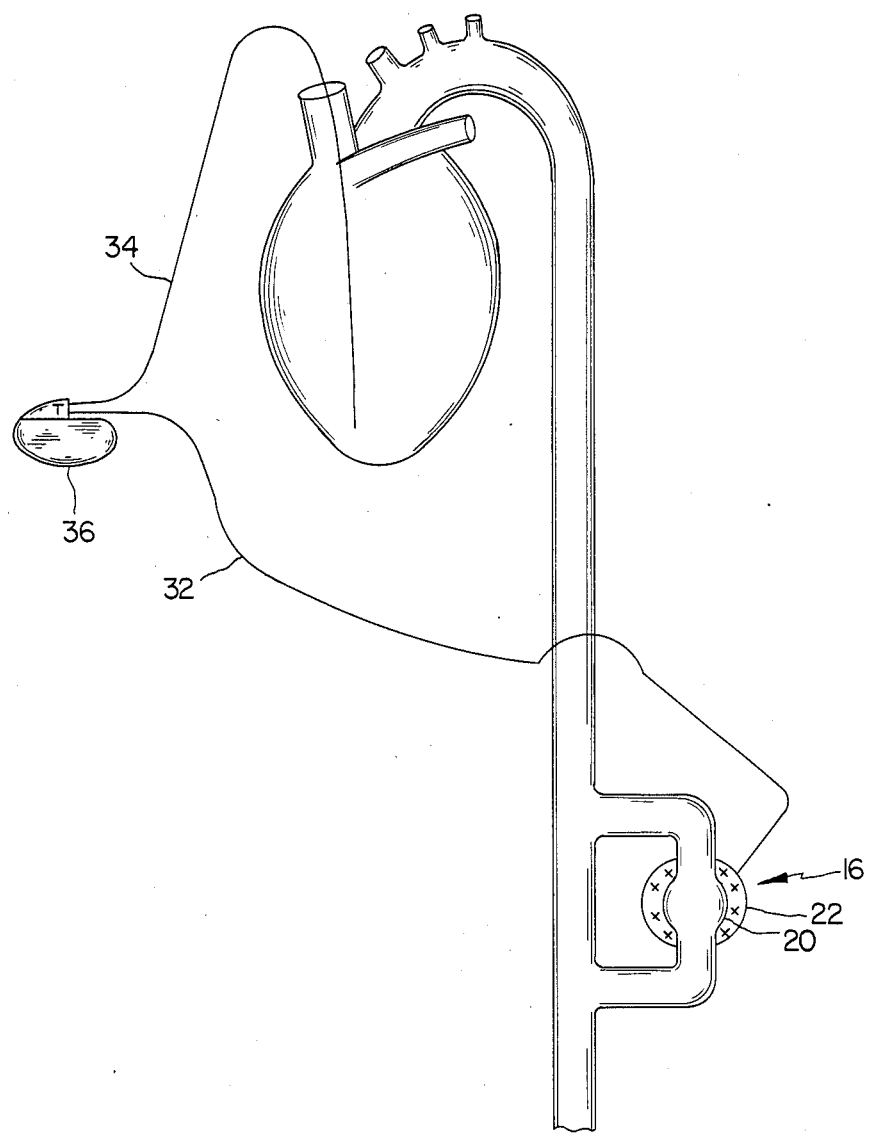
FIG. 4 is a cross-section of an extra aortic balloon counterpulsation embodiment of the invention.

The pumping chamber here needs no entrance or exit valves as shown in FIG. 2 at 14 and in FIG. 4 at 16. The EABC chamber is connected directly to the divided left subclavian artery distal to the thoracodorsal and thoracoacromial branches. A series (T-connection) 14 or parallel (U-connection) 12, 16 pump can be used. The balloon can either be wrapped by the rectus abdominus and latissimus dorsi pedicles, or placed deep to the pectoralis major.

The powering muscle would be stimulated directly by two wire electrodes 32. The stimulator is triggered from the left ventricular electrocardiogram via lead 34 or from the arterial pressure tracing output. Unlike the AACS, in this embodiment the pump would be triggered at the end diastolic phase of the cardiac cycle. This allows increased muscle perfusion which occurs while the muscle is relaxed during systole. Thus, fatigue can be considerably minimized, not only by this operational mode, but also by using the optimal stimulation parameters and protocol as with the AACS.

In addition, the hemodynamic requirements for the EABC device are minimal. There are no valve requirements and the balloon volume can be chosen commensurate with the severity of the situation. A balloon volume of 30 to 70 cc is recommended with an optimum size of 50 cc. The only requirement is that the balloon shape be spherical or nearly spherical in order to avoid sharp edges and corners where blood may stagnate.

The EABC system can be made to offset the primary or essential hypertension. This type of high blood pressure is caused by the progressive increase in construction of arteries and arterioles and their decreasing compliance, a phenomena which gradually increases with age. This is to be distinguished from malignant hypertension which arises from hormonal disturbances of the adrenal glands that sit atop of the kidneys or from malfunctioning of the baroreceptors of the carotid sinus which is in the back of the neck.

By adjusting the pressure wave on the extra-aortic balloon, one can augment the systolic pressure by decreasing the diastolic pressure level. Notice that infants average 80/46 in blood pressure at birth which rises to 100/60 during the first ten days, and levels up at 120/70 during adulthood. The following increase seems to be gradual reaching 135/80 in the fifties and 150/85 in the seventies. The borderlines of 160/95 are at best empirical in the sense that they represent a gradual process, and a 50 year-old subject with 160/90 blood pressure is the equivalent of a healthy counterpart who was 135/80 in his fifties and would extrapolate to 160/90 at 90 or 100 years. The invention disclosed herein involves the gradual augmentation of the cardiac output in such a way to compliantly meet this progressive imbalance—with no extra demand from the heart muscle itself.

The pulse generator 36 of the present device must be adapted to provide chronic background stimulation to the innervated autogenous muscle tissue to provide for the maintenance of a high type two fiber population.

To provide for optimization of the stimulation parameters for any given individual it is required that the pulse generator be capable of providing burst stimulation with a burst duration between 150 and 500 milliseconds, with a number of pulses in a burst being less than or equal to 20. The pacemaker should also be capable of providing stimulation pulses at a rate between 0 and 150 beats-per-minute with a pulse width duration of between 150 and 500 microseconds. To provide for adjustable thresholds of the autogenous tissue, it is desirable to have an amplitude adjustable within the range of 0 to 15 volts with constant current output. The device must have an R-wave synchronous or triggered operating mode for stimulating the autogenous muscle in phase with the depolarization of the cardiac tissue for use in configuration 10. The delay from ventricular sense to stimulus should be variable between 20 and 500 milliseconds and be programmable by the attending physician.

It may also be desirable to provide for stimulating the autogenous tissue at a rate proportional to the sinus rhythm of the patient.

What is claimed is:

1. A cardiac assist device for pumping blood from the left ventricle to the aorta of a patient's heart in synchrony with the ventricular depolarization of the patient's heart comprising:

a first tubular shunt having a proximal and distal end for connection to said left ventricle of said heart through said proximal end;

a second tubular shunt having a proximal and distal end for connection to said aorta of said heart;

an elastic pumping chamber having an oblate ellipsoidal shape defined by a horizontal axis and a vertical axis adapted to be substantially completely surrounded by a sheath of innervated autogenous muscle tissue, and having first and second annular apertures located at the periphery of said chamber concentric with said horizontal axis;

a unidirectional aortic valve coupled to said distal end of said first tubular shunt and coupled to said first aperture;

a unidirectional mitral valve coupled to said distal end of second tubular shunt and coupled to said second aperture;

a pulse generator adapted to be coupled to a first and a second electrode for providing low amplitude continuous stimulation pulses for muscle conditioning and for providing contraction stimulation pulses in a timed relationship with the detected depolarization of said ventricle;

wherein said first electrode is adapted to be coupled to said autogenous muscle tissue for stimulation and adapted to be coupled to said pulse generator; and wherein said second electrode is adapted to be coupled to said ventricle for sensing depolarization of ventricular tissues.

2. A cardiac assist device for pumping blood in synchrony with the ventricular depolarization of a patient's heart comprising:

an elastic pumping chamber having an oblate ellipsoidal shape defined by a horizontal axis and a vertical axis wherein said horizontal axis is greater than said vertical axis and is adapted to be substantially completely surrounded by a sheat of innervated autogenous muscle tissue and having a first aperture adapted for connection to the circulatory system of a patient located at the periphery of said chamber concentric with said horizontal axis; and a pulse generator adapted to be coupled to a first and a second electrode for providing low amplitude continuous stimulation pulses for muscle conditioning and for providing contraction stimulation pulses in a timed relationship with detected depolarizations of the ventricle of the patient's heart and wherein said first electrode is adapted to be coupled to said autogenous muscle tissue for stimulation and adapted to be coupled to said pulse generator; and wherein said second electrode is adapted to be coupled to said ventricle for sensing depolarizations of said ventricle.

3. The device of claim 1 or claim 2 wherein said chamber has a volume greater than 100 ml but less than 200 ml.

4. The device of claim 1 wherein said first tubular shunt has an internal diameter between 1.5 cm and 2.5 cm.

5. The device of claim 1 or claim 4 wherein said second tubular shunt has an internal diameter between 1.1 cm and 2.1 cm.

6. The device of claim 1 or claim 2 wherein the length of the vertical minor axis (b) and horizontal axis (a) bear the relationship: $b = 5.78/a^{\frac{1}{2}}$.

7. The device of claim 1 or claim 2 wherein the muscle mass, m, required to wrap said chamber is greater than 350 gm and less than 600 gm.

8. The device of claim 1 or claim 2 wherein said muscle conditioning stimulating pulses are produced at a frequency greater than 20 Hz and less than 50 Hz.

* * * * *

UNITED STATES PATENT AND TRADEMARK OFFICE
CERTIFICATE OF CORRECTION

PATENT NO. : 4,813,952

DATED : March 21, 1989

INVENTOR(S) : Khalafalla, Aida S.

Figure 3:
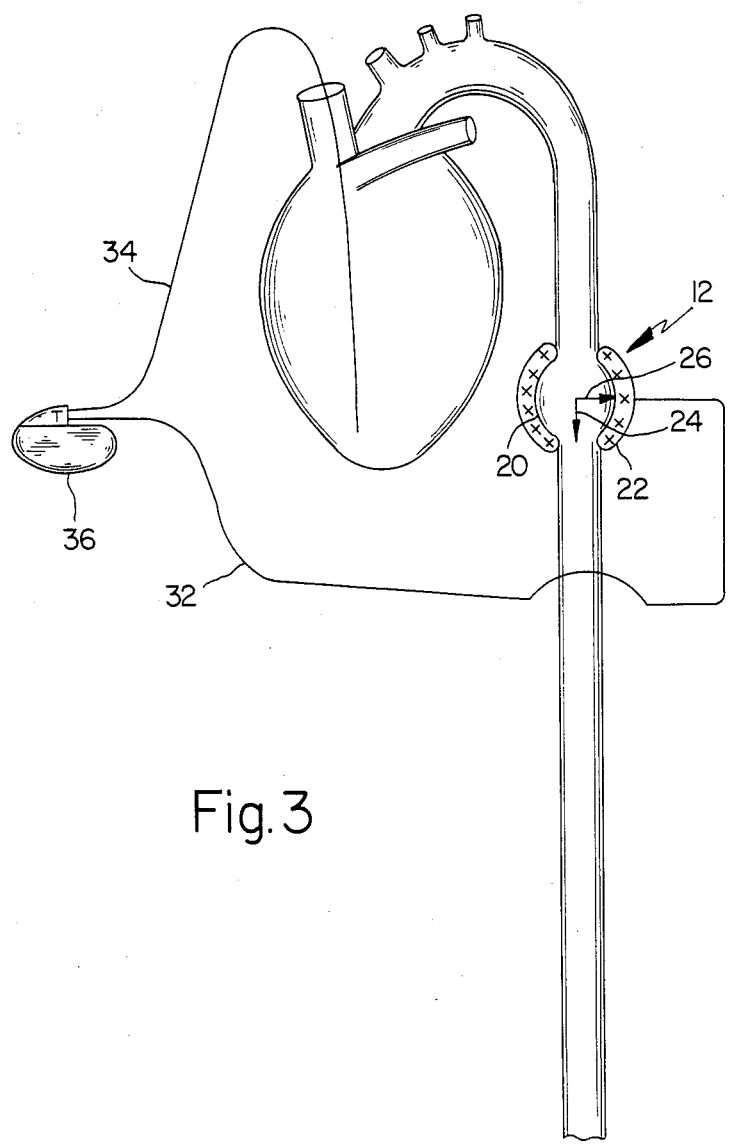
FIG. 3 is a cross-section of an extra aortic balloon counterpulsation embodiment of the invention.

It is certified that error appears in the above-identified patent and that said Letters Patent is hereby corrected as shown below:

Column 3,
  Line 49, --shown only on Fig. 3 -- should be inserted after "axis 24";

Column 5,
  Line 3, "$10^{313}$" should be --$10^{-3}$--.

Signed and Sealed this

Fifth Day of November, 1991

*Attest:*

HARRY F. MANBECK, JR.

*Attesting Officer*      *Commissioner of Patents and Trademarks*